(12) United States Patent
Kitamura

(10) Patent No.: US 9,091,665 B2
(45) Date of Patent: Jul. 28, 2015

(54) TERAHERTZ SPECTROMETRY DEVICE AND METHOD, AND NONLINEAR OPTICAL CRYSTAL INSPECTION DEVICE AND METHOD

(71) Applicant: ARKRAY, Inc., Kyoto (JP)

(72) Inventor: Shigeru Kitamura, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 145 days.

(21) Appl. No.: 13/975,502

(22) Filed: Aug. 26, 2013

(65) Prior Publication Data

US 2014/0061474 A1 Mar. 6, 2014

(30) Foreign Application Priority Data

Aug. 30, 2012 (JP) ................. 2012-190276
Aug. 14, 2013 (JP) ................. 2013-168673

(51) Int. Cl.
| | | |
|---|---|---|
| G01N 21/95 | (2006.01) | |
| G01J 3/42 | (2006.01) | |
| G01J 3/02 | (2006.01) | |
| G01N 21/3581 | (2014.01) | |
| G01N 21/63 | (2006.01) | |

(52) U.S. Cl.
CPC ............. *G01N 21/95* (2013.01); *G01J 3/027* (2013.01); *G01J 3/42* (2013.01); *G01N 21/3581* (2013.01); *G01N 21/636* (2013.01); *G02F 2203/13* (2013.01)

(58) Field of Classification Search
CPC ......... G01N 21/95; G01N 21/351; G01J 3/42; G01J 3/027
See application file for complete search history.

(56) References Cited

U.S. PATENT DOCUMENTS

| | | | |
|---|---|---|---|
| 7,259,859 B2 * | 8/2007 | Pepper .................. | 356/451 |
| 7,894,126 B2 * | 2/2011 | Gunter et al. ........... | 359/328 |
| 2005/0162658 A1 | 7/2005 | Pepper | |

(Continued)

FOREIGN PATENT DOCUMENTS

| | | |
|---|---|---|
| JP | H05-029695 A | 2/1993 |
| JP | 2003-529760 A | 10/2003 |

(Continued)

OTHER PUBLICATIONS

Extended European Search Report issued in corresponding European Patent Application No. 13182090.4 dated Nov. 22, 2013.

*Primary Examiner* — David Porta
*Assistant Examiner* — Faye Boosalis
(74) *Attorney, Agent, or Firm* — Morgan, Lewis & Bockius LLP

(57) ABSTRACT

When light beams of two different wavelengths applied from an excitation light source are made incident on a nonlinear optical crystal having a unique nonlinear coefficient, the nonlinear optical crystal generates THz waves resulting from difference frequency generation according to the nonlinear coefficient that the crystal itself has and SHG waves in which the light beams of two different wavelengths have been wavelength converted in accordance with the nonlinear coefficient. The generated THz waves pass through or are reflected from a sample and are detected by a THz detector. The SHG waves are detected by a SHG detector. A control unit acquires THz measurement values T from the THz detector, acquires SHG measurement values S from the SHG detector, and uses baseline THz measurement values TB and baseline SHG measurement values SB acquired without the sample to perform baseline correction using (T/S)/(TB/SB).

11 Claims, 11 Drawing Sheets

(56) References Cited

U.S. PATENT DOCUMENTS

2009/0303574 A1   12/2009  Gunter et al.
2011/0235163 A1*  9/2011  Ishihara et al. ............... 359/328
2012/0049072 A1*  3/2012  Kajiki et al. ................... 250/351

FOREIGN PATENT DOCUMENTS

| | | |
|---|---|---|
| JP | 2008-268162 A | 11/2008 |
| WO | 2007/121598 A1 | 11/2007 |

* cited by examiner

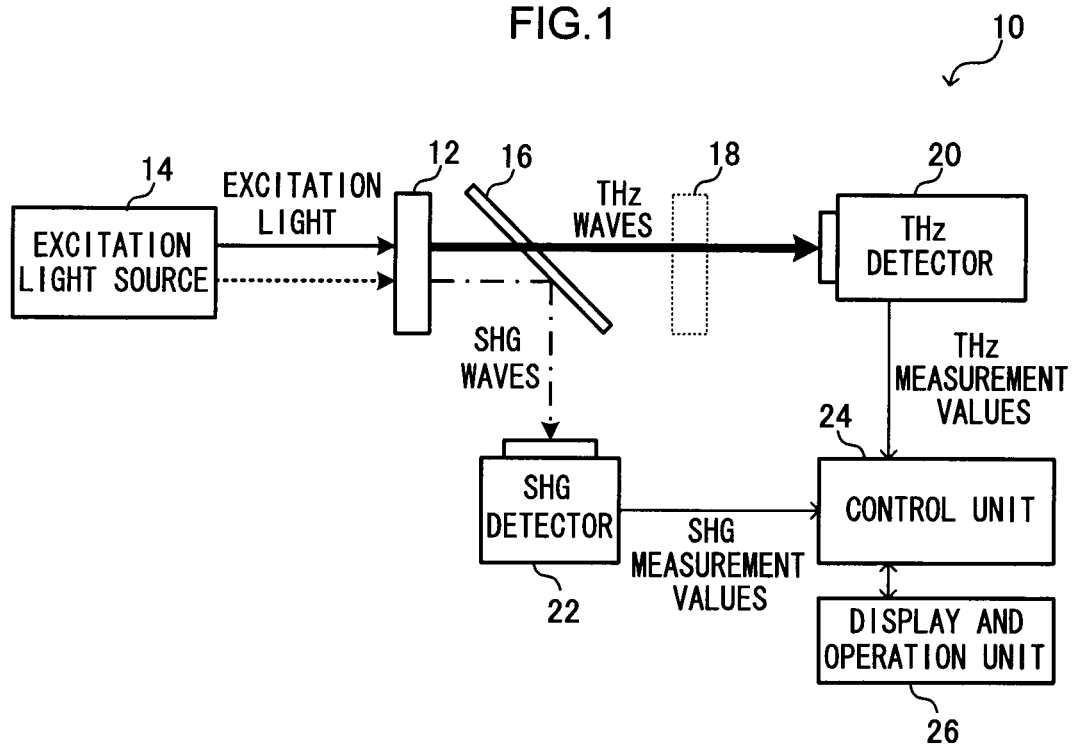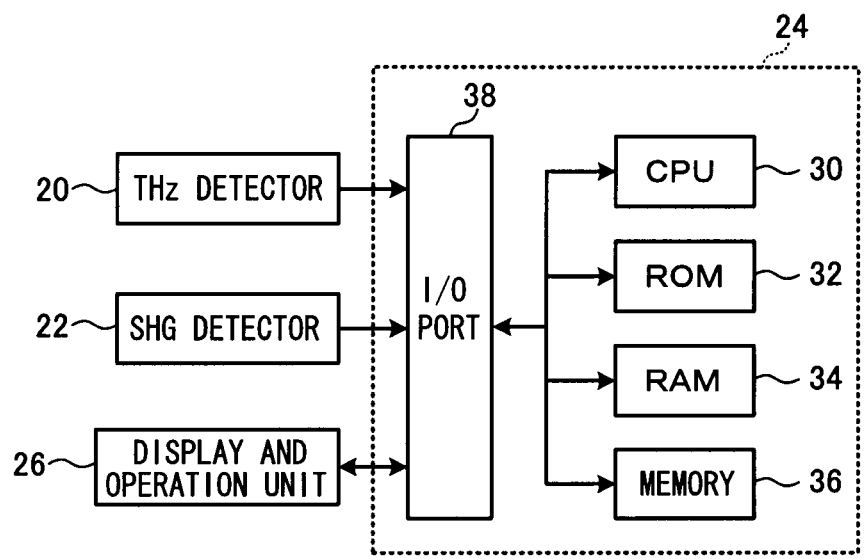

TERAHERTZ SPECTROMETRY DEVICE AND METHOD, AND NONLINEAR OPTICAL CRYSTAL INSPECTION DEVICE AND METHOD

CROSS-REFERENCE TO RELATED APPLICATION

This application is based upon and claims the benefit of priority of Japanese Patent Application No. 2012-190276, filed on Aug. 30, 2012, and the Japanese Patent Application No. 2013-168673, filed on Aug. 14, 2013, the entire contents of which are incorporated herein by reference.

BACKGROUND OF THE INVENTION

1. Field of the Invention

The present invention relates to a terahertz spectrometry device and method and to a nonlinear optical crystal inspection device and method.

2. Description of the Related Art

Conventionally, there has been proposed a frequency sweep terahertz spectrum measurement device which, in the case of frequency calibrating the terahertz spectrum of a measurement sample, separates reference light from terahertz light applied to the sample while performing a frequency sweep and performs intensity correction of the terahertz light to be applied (e.g., see Japanese Patent Application Laid-Open (JP-A) No. 2008-268162).

There has also been proposed an apparatus for investigating a sample, the apparatus comprising: an emitter for irradiating the sample with a beam of emitted electromagnetic radiation; and a detector for detecting the radiation reflected from the sample, wherein there is an optically nonlinear member which functions as both an active part of the emitter and an active part of the detector, said emitter and detector using the same part of the optically nonlinear member (e.g., see JP-A No. 2003-529760). In the apparatus of JP-A No. 2003-529760, targeting reflection measurement, the optical paths for the application and detection of the terahertz waves are made the same and a terahertz reflection mirror is installed on the application optical path, whereby terahertz waves are generated and detected and reference light is acquired.

Further, it is known that, in a semiconductor laser excitation laser device, an intensity of laser output light that is output from the laser device changes according to a wavelength or intensity of excitation light. In this regard, a semiconductor laser excitation laser device has been proposed, in which an intensity of laser output light is detected, and in accordance with the value thereof, a driving current and a temperature of a semiconductor laser for excitation is controlled so as to stabilize the intensity of the laser output light (e.g., see JP-A No. H05-029695).

Generally, in order to raise measurement sensitivity in spectral analysis, it is extremely important to improve the signal-to-noise ratio (S/N ratio)—that is, to increase signal strength and reduce noise. Further, in order to raise measurement reproducibility, it is important to perform intensity correction of the measurement light taking changes in the intensity of the light of the light source as a reference. This also applies to terahertz spectral analysis, and a high-intensity terahertz light source and intensity correction of the measurement light are essential.

However, the technology of JP-A No. 2008-268162 acquires the reference light for performing intensity correction of the terahertz measurement light by separating it from the terahertz light source. This means that the intensity of the terahertz waves applied to the measurement object—that is, the intensity of the light of the light source—drops, and there is the problem that the technology cannot realize a high-intensity terahertz light source, which is one factor for realizing high sensitivity and high reproducibility in spectral analysis.

Further, even in a case where the light of the light source is laser output light, a portion of the laser output light that has been output from the laser device is taken out in the technology of JP-A No. H05-029695 in order to stabilize the intensity of the laser output light, and the problem that the intensity of the light of the light source irradiated to the measurement object drops similarly exists even in the case where the light of the light source is laser output light. In particular, because terahertz waves by nature are weak in intensity, when the reference light is separated from the terahertz light source, the drop in the intensity of the terahertz light source ends up becoming pronounced.

Further, in a method that separates the reference light from the terahertz light source like in the technology of JP-A No. 2008-268162, two detectors for detecting the terahertz waves—a detector that detects the terahertz waves that have passed through or been reflected from the measurement object and a detector that detects the terahertz waves that have been separated as the reference light—become necessary, and there is also a problem in terms of cost because terahertz detectors are expensive.

Further, the technology of JP-A No. 2003-529760 detects the detection light and the reference light on the same optical path by inserting the terahertz reflection mirror, so the detector for detecting the terahertz waves can be configured by a single detector. However, the technology of JP-A No. 2003-529760 has the problem that it cannot perform intensity correction with good precision because the timings when the detection light and the reference light are acquired differ.

SUMMARY OF THE INVENTION

The present invention has been made in order to solve the above problems, and it is an object thereof to provide a terahertz spectrometry device and method that can perform intensity correction of terahertz measurement values with good precision without lowering the intensity of terahertz waves to be generated and a nonlinear optical crystal inspection device and method that can inspect the condition of a nonlinear optical crystal used for measurement.

In order to achieve the above object, a terahertz spectrometry device of the present invention is configured to include: a nonlinear optical crystal that has a unique nonlinear coefficient and generates, from light beams of two different wavelengths made incident thereon, terahertz waves resulting from sum frequency generation or difference frequency generation according to the nonlinear coefficient and optical harmonics in which the light beams of two different wavelengths have been wavelength converted in accordance with the nonlinear coefficient; first detecting means that directly detects the terahertz waves generated from the nonlinear optical crystal or detects measurement terahertz waves that have passed through or been reflected from a measurement target to which the terahertz waves have been applied; second detecting means that detects at least one of the optical harmonics generated from the nonlinear optical crystal; and measuring means that obtains measurement values in which an intensity of the measurement terahertz waves detected by the first detecting means has been corrected on the basis of an intensity of the at least one optical harmonic detected by the second detecting means.

According to the terahertz spectrometry device of the present invention, when the light beams of two different wavelengths are made incident as excitation light on the nonlinear optical crystal having the unique nonlinear coefficient, the nonlinear optical crystal generates terahertz waves resulting from sum frequency generation or difference frequency generation according to the nonlinear coefficient that the crystal itself has and optical harmonics in which the light beams of two different wavelengths have been wavelength converted in accordance with the nonlinear coefficient. The terahertz waves generated from the nonlinear optical crystal are detected by the first detecting means directly or as measurement terahertz waves that have passed through or been reflected from the measurement target to which the terahertz waves have been applied. Further, at least one of the optical harmonics generated from the nonlinear optical crystal is detected by the second detecting means. Additionally, the measuring means obtains measurement values in which the intensity of the measurement terahertz waves detected by the first detecting means has been corrected on the basis of the intensity of the at least one optical harmonic detected by the second detecting means.

In this way, by correcting the intensity of the terahertz waves using the intensity of the optical harmonics that have not been utilized in conventional terahertz measurement systems and which are generated in accordance with the same nonlinear coefficient as the terahertz waves, intensity correction of the terahertz measurement values can be performed with good precision without lowering the intensity of the terahertz waves to be generated.

Further, the measuring means can acquire, as baseline terahertz waves, terahertz waves directly detected by the first detecting means, acquire, as a baseline optical harmonic, an optical harmonic detected at the same time as the baseline terahertz waves, and obtain the corrected measurement values on the basis of a relationship between the baseline terahertz waves, the baseline optical harmonic, the measurement terahertz waves, and the optical harmonic detected at the same time as the measurement terahertz waves. By performing this baseline correction, appropriate intensity correction can be performed.

Further, the optical harmonic is a second harmonic of the light beams of two different wavelengths.

Further, the measuring means can obtain the measurement values using the measurement terahertz waves detected by applying the terahertz waves generated from the nonlinear optical crystal to the measurement target while performing a frequency sweep or the measurement terahertz waves detected by applying terahertz waves of a specific frequency generated from the nonlinear optical crystal to the measurement target. In this way, the present invention can be applied regardless of the measurement method.

Further, the terahertz spectrometry device of the present invention can be configured to further include determining means that determines whether or not there is damage to the nonlinear optical crystal on the basis of a correlation between the intensity of the measurement terahertz waves detected by the first detecting means and the intensity of the at least one optical harmonic detected by the second detecting means. The terahertz waves and the optical harmonic generated in accordance with the nonlinear coefficient that the nonlinear optical crystal has show a strong correlation if the nonlinear optical crystal is in a normal condition, so whether or not there is damage to the nonlinear optical crystal can be determined on the basis of the correlation between the intensity of the terahertz waves and the intensity of the optical harmonic.

For example, the determining means can determine that there is damage to the nonlinear optical crystal in a case where an absolute value of a correlation coefficient, or a coefficient of determination, between the intensity of the measurement terahertz waves detected by the first detecting means and the intensity of the at least one optical harmonic detected by the second detecting means is smaller than a predetermined threshold value.

Further, for example, the determining means can determine that there is damage to the nonlinear optical crystal in a case where a difference between an absolute value of a correlation coefficient, or a coefficient of determination, between the intensity of the measurement terahertz waves detected by the first detecting means and the intensity of the at least one optical harmonic detected by the second detecting means and an absolute value of a correlation coefficient, or a coefficient of determination, obtained using the nonlinear optical crystal in a normal condition is larger than a predetermined threshold value.

Further, the terahertz spectrometry device of the present invention can be configured to further include determining means that determines that there is damage to the nonlinear optical crystal in a case where a difference between either one intensity of the intensity of the measurement terahertz waves detected by the first detecting means and the intensity of the at least one optical harmonic detected by the second detecting means, a computed value representing the other intensity obtained on the basis of a relational equation between the intensity of the measurement terahertz waves and the intensity of the at least one optical harmonic obtained using the nonlinear optical crystal in a normal condition, and the other intensity that has been detected is larger than a predetermined threshold value. By using this determining means also, whether or not there is damage to the nonlinear optical crystal can be determined.

Further, a terahertz spectrometry method of the present invention is a method which: detects measurement terahertz waves that have passed through or been reflected from a measurement target to which have been applied terahertz waves generated from a nonlinear optical crystal that has a unique nonlinear coefficient and generates, from light beams of two different wavelengths made incident thereon, terahertz waves resulting from sum frequency generation or difference frequency generation according to the nonlinear coefficient and optical harmonics in which the light beams of two different wavelengths have been wavelength converted in accordance with the nonlinear coefficient; detects at least one of the optical harmonics generated from the nonlinear optical crystal; and obtains measurement values in which an intensity of the measurement terahertz waves that have been detected has been corrected on the basis of an intensity of the at least one optical harmonic that has been detected.

Further, a nonlinear optical crystal inspection device of the present invention is configured to include: a nonlinear optical crystal that has a unique nonlinear coefficient and generates, from light beams of two different wavelengths made incident thereon, terahertz waves resulting from sum frequency generation or difference frequency generation according to the nonlinear coefficient and optical harmonics in which the light beams of two different wavelengths have been wavelength converted in accordance with the nonlinear coefficient; first detecting means that directly detects the terahertz waves generated from the nonlinear optical crystal or detects measurement terahertz waves that have passed through or been reflected from a measurement target to which the terahertz waves have been applied; second detecting means that detects at least one of the optical harmonics generated from the nonlinear optical crystal; and determining means that determines whether or not there is damage to the nonlinear optical crystal on the basis of a correlation between an intensity of the measurement terahertz waves detected by the first detecting means and an intensity of the at least one optical harmonic detected by the second detecting means.

Further, a nonlinear optical crystal inspection method of the present invention is an inspection method which: detects measurement terahertz waves that have passed through or been reflected from a measurement target to which have been applied terahertz waves generated from a nonlinear optical crystal that has a unique nonlinear coefficient and generates, from light beams of two different wavelengths made incident thereon, terahertz waves resulting from sum frequency generation or difference frequency generation according to the nonlinear coefficient and optical harmonics in which the light beams of two different wavelengths have been wavelength converted in accordance with the nonlinear coefficient; detects at least one of the optical harmonics generated from the nonlinear optical crystal; and determines whether or not there is damage to the nonlinear optical crystal on the basis of a correlation between an intensity of the measurement terahertz waves that have been detected and an intensity of the at least one optical harmonic that has been detected.

According to the nonlinear optical crystal inspection device and method of the present invention, the condition of the nonlinear optical crystal used for measurement can be inspected on the basis of the correlation between the intensity of the measurement terahertz waves and the intensity of the optical harmonic.

As described above, according to the terahertz spectrometry device and method of the present invention, there is obtained the effect that, by correcting the intensity of the terahertz waves using the intensity of the optical harmonics that have not been utilized in conventional terahertz measurement systems and which are generated in accordance with the same nonlinear coefficient as the terahertz waves, intensity correction of the terahertz measurement values can be performed with good precision without lowering the intensity of the terahertz waves to be generated.

Further, according to the nonlinear optical crystal inspection device and method of the present invention, the condition of the nonlinear optical crystal used for measurement can be inspected on the basis of the correlation between the intensity of the measurement terahertz waves and the intensity of the optical harmonic.

BRIEF DESCRIPTION OF THE DRAWINGS

FIG. 1 is a schematic diagram showing the configuration of a terahertz spectrometry device pertaining to a first embodiment;

FIG. 2 is a block diagram showing the configuration of a control unit;

DESCRIPTION OF EMBODIMENTS

Figure 3:
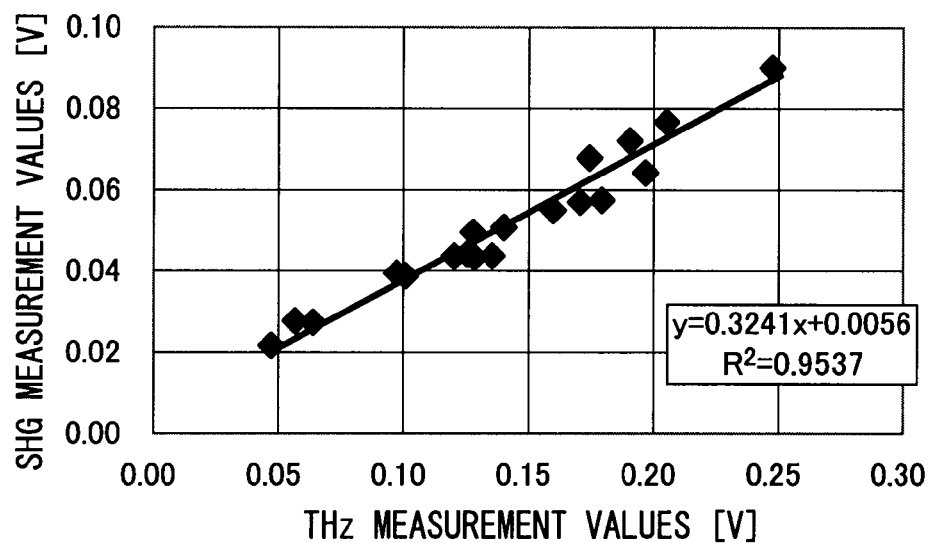
FIG. 3 is a graph showing the correlation between THz measurement values and SHG measurement values.

Embodiments of the present invention will be described in detail below with reference to the drawings.

As shown in FIG. 1, a terahertz spectrometry device 10 pertaining to the present embodiment is configured to include a nonlinear optical crystal 12 that has a unique nonlinear coefficient, an excitation light source 14 that generates excitation light beams of two different wavelengths made incident on the nonlinear optical crystal 12, a filter 16 that separates terahertz waves (abbreviated as "THz waves" below) and second harmonics (abbreviated as "SHG waves" below) generated from the nonlinear optical crystal 12, a measurement stage 18 on which a measurement target sample is set, a THz detector 20 that detects the THz waves, a SHG detector 22 that detects the SHG waves, a control unit 24 that executes processing for spectral measurement of the THz waves, and a display and operation unit 26 with which various types of information are input as a result of the display and operation unit 26 being operated and which is configured by a touch panel display or the like for displaying measurement results and so forth. The THz detector 20 is an example of first detecting means of the present invention, the SHG detector 22 is an example of second detecting means of the present invention, and the control unit 24 is an example of measuring means of the present invention.

The nonlinear optical crystal 12 generates, from the excitation light beams of two different wavelengths made incident from the excitation light source 14, the THz waves by sum frequency generation or difference frequency generation according to the nonlinear coefficient that the nonlinear optical crystal 12 has. Further, at the same time as when the nonlinear optical crystal 12 generates the THz waves, the nonlinear optical crystal 12 generates the SHG waves in which the excitation light beams of two wavelengths made incident have been wavelength converted in accordance with the nonlinear coefficient. For example, in a case where the frequencies of the excitation light beams of two wavelengths are $\omega_1$ and $\omega_2$, the nonlinear optical crystal 12 generates THz waves having a frequency $\omega_3$ equal to $|\omega_1+\omega_2|$ or $|\omega_1-\omega_2|$ and also generates SHG waves having frequencies $2\omega_1$ and $2\omega_2$. As the nonlinear optical crystal 12, for example DAST (4-dimethylamino-N-methyl-4-stilbazolium tosylate) crystal or DASC (4-dimethylamino-N-methyl-4-stilbazolium p-chlorobenzenesulfonate) crystal can be used.

As the excitation light source 14, for example, a two wavelength generating semiconductor laser that can generates light beams of two different wavelengths can be used.

As the filter 16, a dichroic filter that allows light in the frequency band of the THz waves to pass through it and reflects light in the frequency band of the SHG waves can be used. It suffices provided that the filter 16 can separate the THz waves and the SHz waves.

The THz detector 20 detects the THz waves and outputs electrical signals according to the intensity of the detected THz waves as THz measurement values. As the THz detector 20, for example, a pyroelectric detector can be used.

The SHG detector 22 detects the SHG waves and outputs electrical signals according to the intensity of the detected SHG waves as SHG measurement values. As the SHG detector 22, for example, a silicon (Si) bolometer can be used. As described above, SHG waves having the two frequencies of $2\omega_1$ and $2\omega_2$ are generated, but the SHG detector 22 may be configured to detect either of the two frequencies of the SHG waves or may be configured to detect the two frequencies of the SHG waves and output the sum of the intensities of the SHG waves as the SHG measurement values.

As shown in FIG. 2, the control unit 24 is configured by a computer including a CPU 30 that controls the entire terahertz spectrometry device 10, a ROM 32 serving as a storage medium that stores a program for executing terahertz spectrometry processing including baseline correction value calculation processing and sample measurement processing described later, a RAM 32 that temporarily stores data as a work area, a memory 36 serving as storage means in which various types of information are stored, an input/output port (I/O port) 38, and a bus that interconnects these. The control unit 24 may further include a HDD serving as storage means. The THz detector 20, the SHG detector 22, and the display and operation unit 26 are connected to the I/O port 38.

Here, the principle of the present embodiment will be described.

The terahertz spectrometry device 10 pertaining to the present embodiment uses the SHG waves detected by the SHG detector 22 as reference light to perform intensity correction of the THz measurement values. The SHG waves are light that is unnecessary in terahertz measurement systems and conventionally have been cut by a filter, for example, and not utilized. For that reason, even if the SHG waves are acquired as reference light, the intensity of the THz waves generated from the nonlinear optical crystal 12 does not drop.

Further, fluctuations occur in the intensity of the THz waves generated from the nonlinear optical crystal 12 due to factors indicated below.

(a) Fluctuations in the output value of the excitation light (b) Partial disruptions in the crystal structure included in the nonlinear optical crystal 12, and dislocations and lattice defects within the crystal structure (c) The thermal lens effect, which occurs in the nonlinear optical crystal 12 when the excitation light is applied (d) Changes in the amount of heat accumulated in the nonlinear optical crystal 12 in accompaniment with the elapse of the application time of the excitation light resulting from fluctuations in the output value of the excitation light Fluctuations in the intensity of the THz waves affect the THz measurement values that are measured, so it is necessary to perform intensity correction of the THz measurement values taking the above factors into consideration.

Here, in order to suppress a drop in the intensity of the THz waves to be generated, it is also conceivable to acquire, as the reference light, the excitation light (fundamental waves) that has passed through the nonlinear optical crystal 12, for example, rather than separating the THz waves themselves. However, in this case, the fundamental waves are not light that has been wavelength converted in accordance with the nonlinear coefficient of the nonlinear optical crystal 12, so although fluctuations in the intensity of the THz waves resulting from factor (a) can be eliminated, fluctuations in the intensity of the THz waves whose factors are the structure of the nonlinear optical crystal 12 and so forth, like (b) to (d), cannot be eliminated.

The THz waves and the SHG waves are generated in accordance with the same nonlinear coefficient of the nonlinear optical crystal 12, so fluctuations that are in alignment with the fluctuations in the THz waves resulting from factors such as (b) to (d) also occur in the SHG waves. FIG. 3 shows a graph in which THz measurement values and SHG measurement values, which have been measured at the same time while changing the excitation light output to vary the intensity of the THz waves generated from the nonlinear optical crystal 12, have been plotted taking the THz measurement values (voltage values [V]) on the X axis and the SHG measurement values (voltage values [V]) on the Y axis. As shown in FIG. 3, it will be understood that there is a proportional correlation between the THz measurement values and the SHG measurement values.

In this way, by using the SHG waves that have not conventionally been utilized, intensity correction of the THz measurement values corresponding to the fluctuations in the intensity of the THz waves that occur due to various factors can be performed without lowering the intensity of the THz waves.

Next, the principle of intensity correction of the THz measurement values using the SHG waves will be described.

Figure 4:
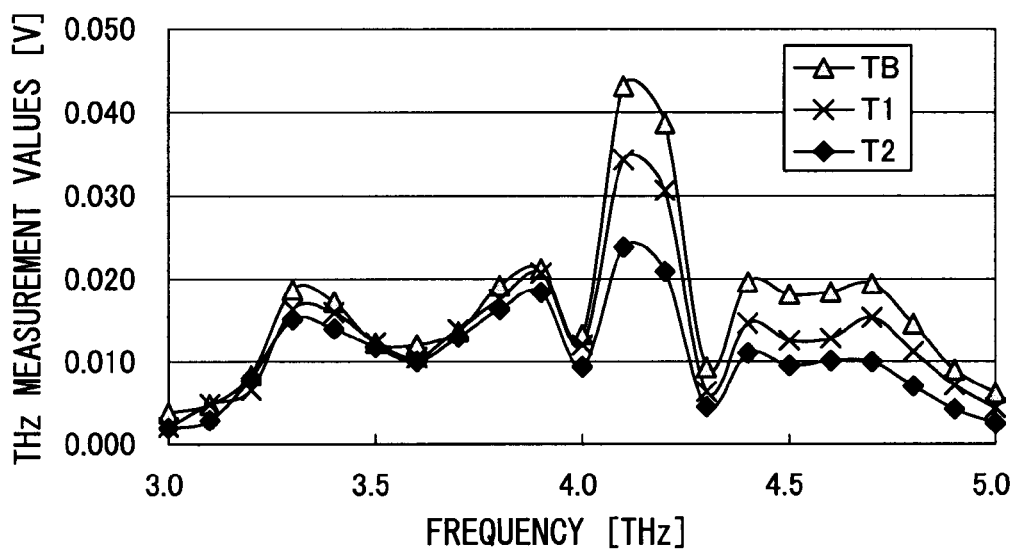
FIG. 4 is a graph showing THz measurement values with respect to a frequency sweep.

FIG. 4 shows measurement results of frequency-THz measurement values when a frequency sweep of the THz waves has been performed in each of a case where the output of the excitation light has been fixed and a case where the output of the excitation light has been varied. The frequency-THz measurement values in the case where the output of the excitation light was fixed are denoted by baseline THz measurement values TB, and the measurement commencement time is denoted by t0. Further, the variations in the excitation light output assume light source drift in the terahertz light source, and as frequency-THz measurement values in the case where the output of the excitation light was varied, THz measurement values T1 at a measurement commencement time t1 (t1>t0) and THz measurement values T2 at a measurement commencement time t2 (t2>t1) were measured. As shown in FIG. 4, in a case where light source drift has occurred, the drop in the THz measurement values becomes pronounced at frequencies from 4 THz on.

Further, in conventional terahertz measurement systems (single beam systems), before measurement with respect to the measurement target sample, a frequency sweep such as described above is performed to measure the baseline THz measurement values TB, and single beam correction is performed taking T/TB with respect to THz measurement values T at the time of sample measurement.

Figure 5:
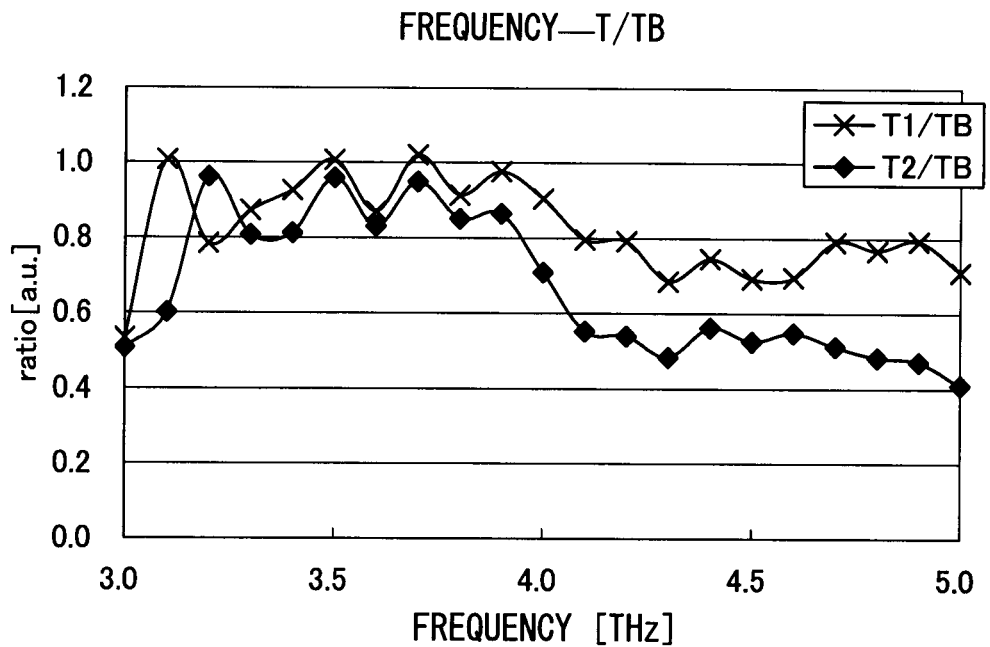
FIG. 5 is a graph showing THz measurement values on which conventional baseline correction has been performed.

FIG. 5 shows results in which the measurement results of FIG. 4 have been applied to these correction values. TB, T1, and T2 are all values that have been measured without the sample, so the fitness values of the correction values should be in the vicinity of 1, but as shown in FIG. 5, in a case where light source drift has occurred, a misalignment occurs between the correction values and the fitness values. Further, a misalignment of the correction values also occurs between T1/TB and T2/TB, and this shows that, because fluctuations in the intensity of the THz waves occur due to various factors, the condition of the fluctuations also differs for each measurement, causing misalignment of the measurement values.

Consequently, conventional baseline correction cannot correct misalignment of the measurement values resulting from fluctuations in the terahertz waves that have occurred due to various factors.

In the present embodiment, on the basis of the fact that the correlation between the SHG waves and the THz waves is strong, that is, on the basis of the fact that the SHG waves fluctuate in alignment with the THz waves, SHG measurement values S are used to perform intensity correction of the THz measurement values T using the following equation (1).

$$\text{THz measurement value intensity correction equation} = T/S \quad (1)$$

Here, T and S are measurement values that have been measured at the same time.

Figure 6:
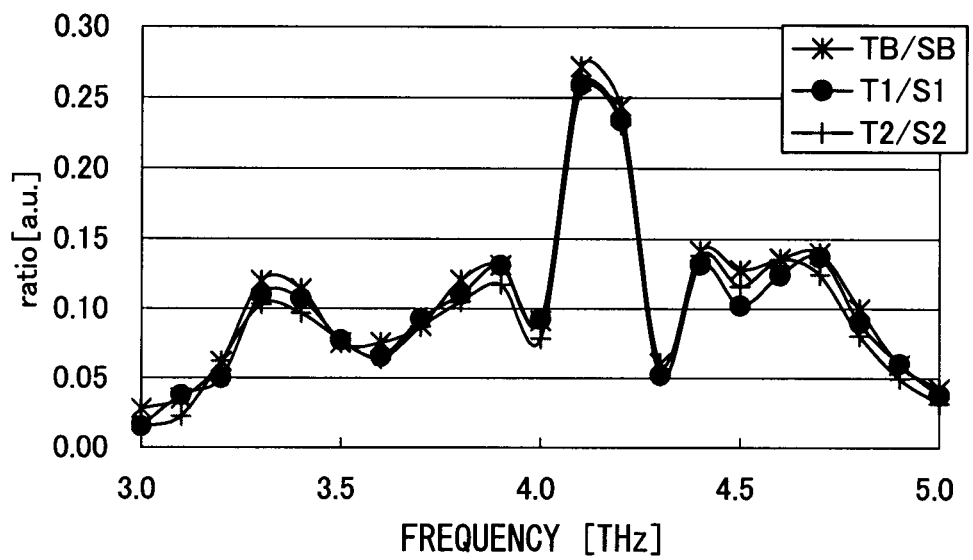
FIG. 6 is a graph showing THz measurement values on which intensity correction in the first embodiment has been performed.

FIG. 6 shows results in which the measurement results shown in FIG. 4 have been corrected using equation (1). As shown in FIG. 6, the drops in the THz measurement values seen in the measurement results of FIG. 4 are eliminated.

Further, using intensity correction equation (1), baseline correction is performed using the following equation (2).

$$\text{Baseline correction equation} = (T/S)/(TB/SB) \quad (2)$$

Here, SB denotes baseline SHG measurement values that have been measured at the same time as baseline THz measurement values TB. Correction equation (2) is an example and may also be used in an appropriately altered form such as $(T/TB)\times(SB/S)$.

Figure 7:
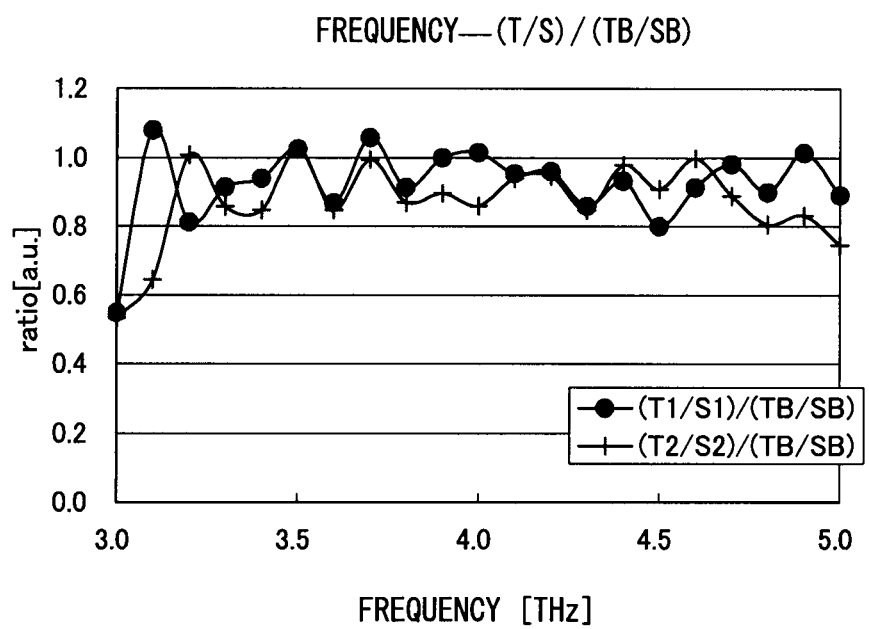
FIG. 7 is a graph showing THZ measurement values on which baseline correction in the first embodiment has been performed.

FIG. 7 shows baseline correction results resulting from equation (2). As shown in FIG. 7, the misalignment between the measurement values and the fitness values (here, 1) and the misalignment between the measurements (here, T1 and T2) seen in the correction results of FIG. 5 are both eliminated.

Next, the working of the terahertz spectrometry device 10 pertaining to the first embodiment will be described. First, the terahertz spectrometry device 10 executes the baseline correction value calculation processing shown in FIG. 8 at a predetermined timing such as before sample measurement when the sample has not been set on the measurement stage 18. Additionally, the terahertz spectrometry device 10 executes the sample measurement processing shown in FIG. 9 at the time of sample measurement when the sample has been set on the measurement stage 18. Each type of processing is performed as a result of the CPU 30 reading out and executing a program stored in the ROM 32. Each type of processing will be described in detail below.

First, in the baseline correction value calculation processing, in step 100, the control unit 24 causes the excitation light beams to be generated from the excitation light source 14, causes the excitation light beams to start to be applied to the nonlinear optical crystal 12, and, in order to perform a frequency sweep of the THz waves, adjusts the excitation light beams in such a way that the difference between the two frequencies varies. At this time, the THz waves and the SHG waves that correlate with the THz waves are generated from the nonlinear optical crystal 12.

Next, in step 102, the control unit 24 causes the THz detector 20 to detect the THz waves generated from the nonlinear optical crystal 12 at each frequency in the frequency sweep and causes the SHG detector 22 to detect the generated SHG waves. Because of this, electrical signals of voltage values according to the intensity of the detected THz waves are output from the THz detector 20, and electrical signals of voltage values according to the intensity of the detected SHG waves are output from the SHG detector 22.

Next, in step 104, the control unit 24 acquires the electrical signals output from the THz detector 20 as the baseline THz measurement values TB and acquires the electrical signals output from the SHG detector 22 as the baseline SHG measurement values SB.

Next, in step 106, the control unit 24 calculates TB/SB for each frequency from the baseline THz measurement values TB and baseline SHG measurement values SB acquired in step 104, saves the values TB/SB in a predetermined storage region of the memory 36 or the like as baseline correction values, and ends the baseline correction value calculation processing.

Next, in the sample measurement processing, in steps 110 and 112, the control unit 24 causes the THz waves and the SHG waves to be generated while performing a frequency sweep and causes the THz detector 20 and the SHG detector 22 to detect the THz waves and the SHG waves, respectively, using processing steps that are the same as steps 100 and 102 of the baseline correction value calculation processing. At this time, the THz waves detected by the THz detector 20 are THz waves that have passed through or been reflected from the sample set on the measurement stage 18.

Next, in step 114, the control unit 24 acquires the electrical signals output from the THz detector 20 as the THz measurement values T and acquires the electrical signals output from the SHG detector 22 as the SHG measurement values S.

Next, in step 116, the control unit 24 reads out the baseline correction values TB/SB from the predetermined storage region and uses the THz measurement values T and SHG measurement values S acquired in step 114 to perform baseline correction using equation (2).

Next, in step 118, the control unit 24 outputs the measurement results corrected in step 116 to the display and operation unit 26 and ends the sample measurement processing. As for the output of the measurement results, for example, the control unit 24 may be configured to have the display and operation unit 26 display a graph of the THz wave optical spectrum expressed by frequency-(T/S)/(TB/SB) or may be configured to identify the sample type by comparing the measured THz wave optical spectrum with THz wave optical spectra per sample type separately stored beforehand and output the identification result.

As described above, according to the terahertz spectrometry device pertaining to the first embodiment, by using, as the reference light, the SHG waves that have not been utilized in conventional terahertz measurement systems and which are generated in accordance with the same nonlinear coefficient as the terahertz waves, intensity correction of the terahertz measurement values can be performed with good precision without lowering the intensity of the terahertz waves to be generated.

For that reason, measurement sensitivity can be improved while maintaining measurement reproducibility.

Next, a second embodiment will be described. In the second embodiment, a case where the terahertz spectrometry device determines whether or not there is damage to the nonlinear optical crystal on the basis of the correlation between the THz waves and the SHG waves and thereafter performs terahertz spectrometry will be described. The configuration of the terahertz spectrometry device pertaining to the second embodiment is the same as the configuration of the terahertz spectrometry device 10 pertaining to the first embodiment, so the same reference signs will be assigned thereto and detailed description thereof will be omitted. The control unit 24 is an example of determining means of the present invention. The working of the terahertz spectrometry device pertaining to the second embodiment will be described below.

Figure 8:
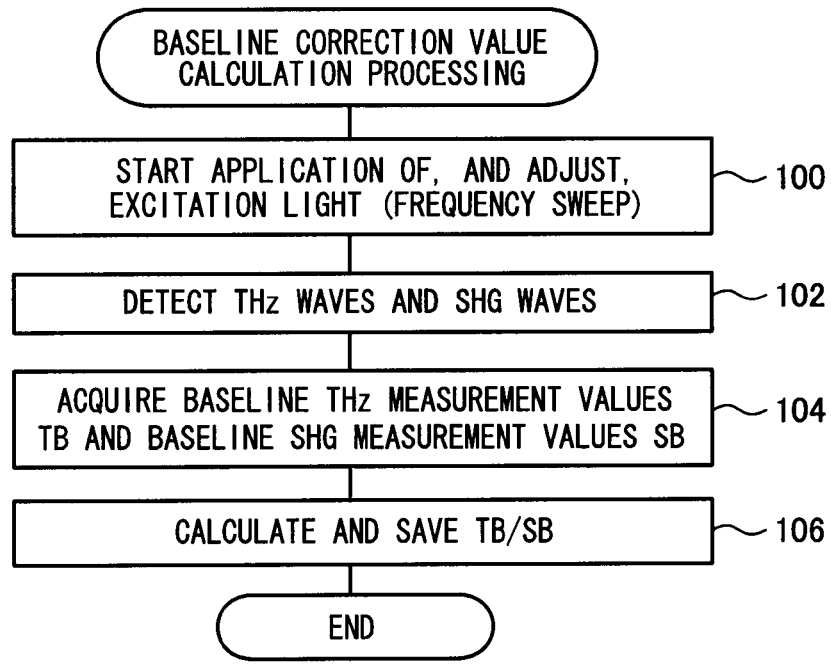
FIG. 8 is a flowchart showing the content of baseline correction value calculation processing in the first embodiment.
Figure 9:
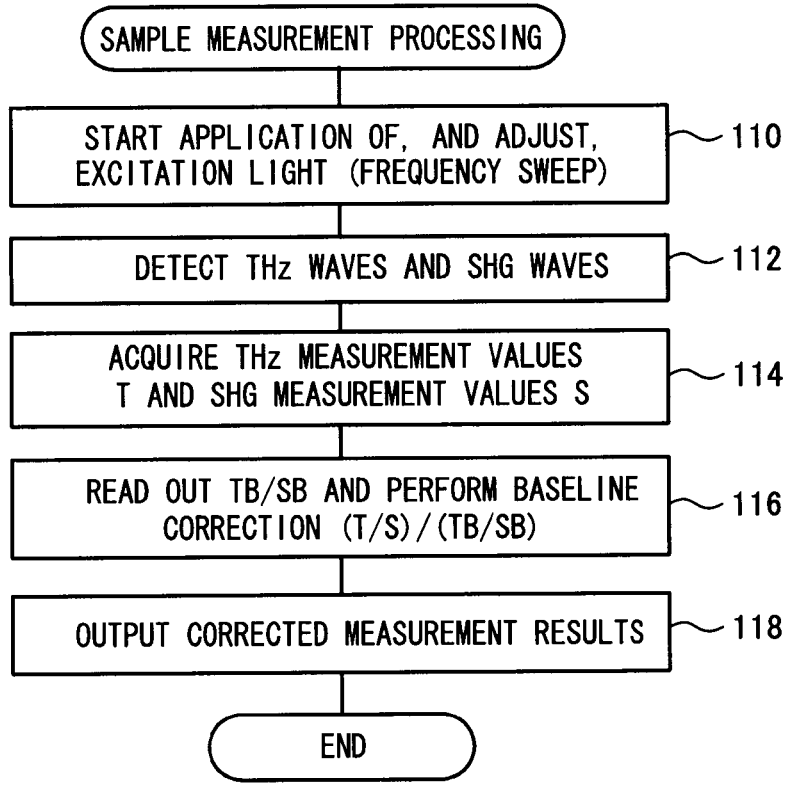
FIG. 9 is a flowchart showing the content of sample measurement processing in the first embodiment.
Figure 10:
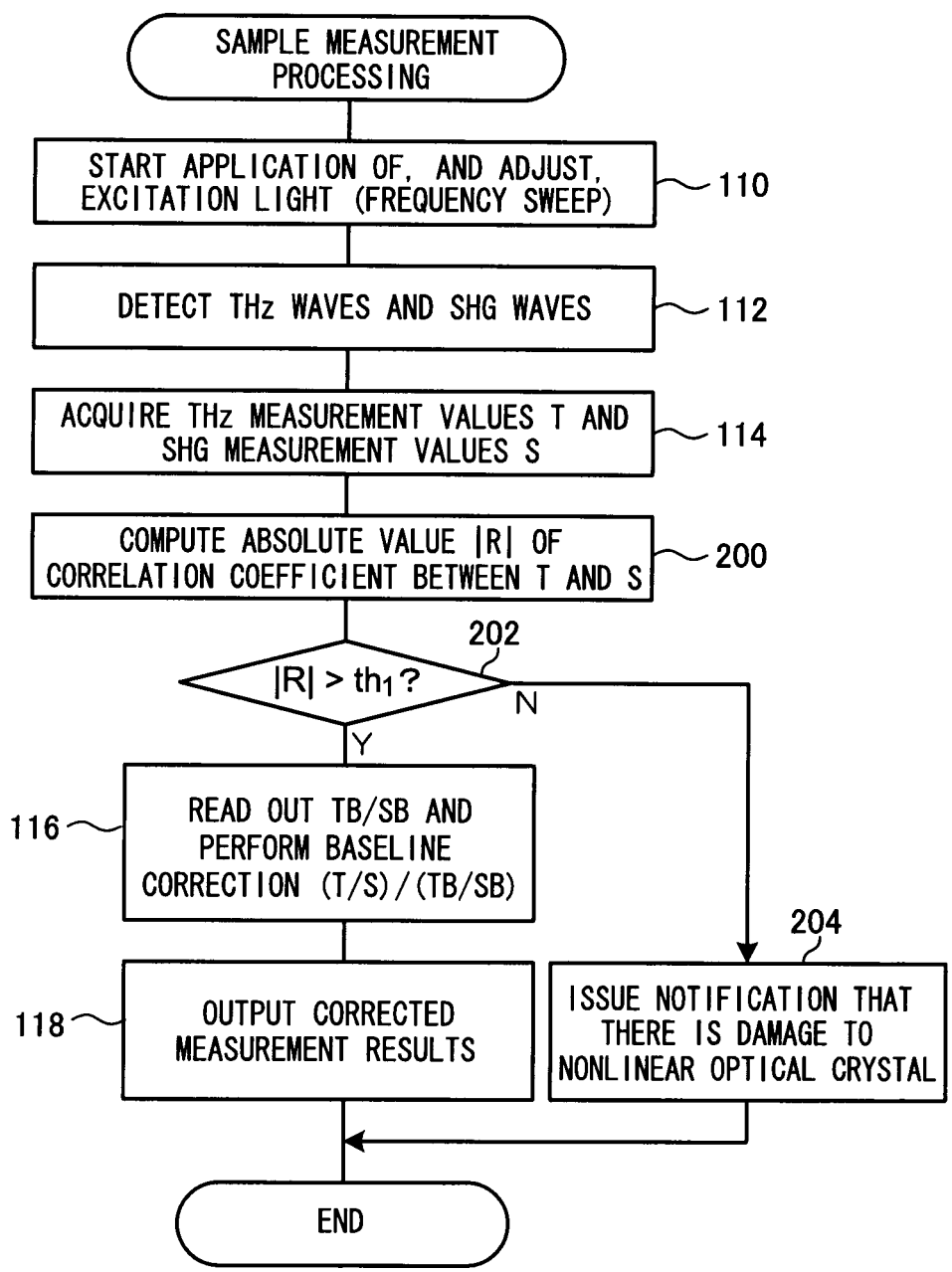
FIG. 10 is a flowchart showing the content of sample measurement processing in a second embodiment.

First, like in the first embodiment, the terahertz spectrometry device executes the baseline correction value calculation processing shown in FIG. 8 at a predetermined timing such as before sample measurement when the sample has not been set on the measurement stage 18. Then, the terahertz spectrometry device executes the sample measurement processing shown in FIG. 10 at the time of sample measurement when the sample has been set on the measurement stage 18. Each type of processing is performed as a result of the CPU 30 reading out and executing a program stored in the ROM 32. The sample measurement processing in the second embodiment will be described in detail below. In regard to processing steps that are the same as those of the sample measurement processing in the first embodiment, the same reference signs will be assigned thereto and detailed description thereof will be omitted.

Figure 11:
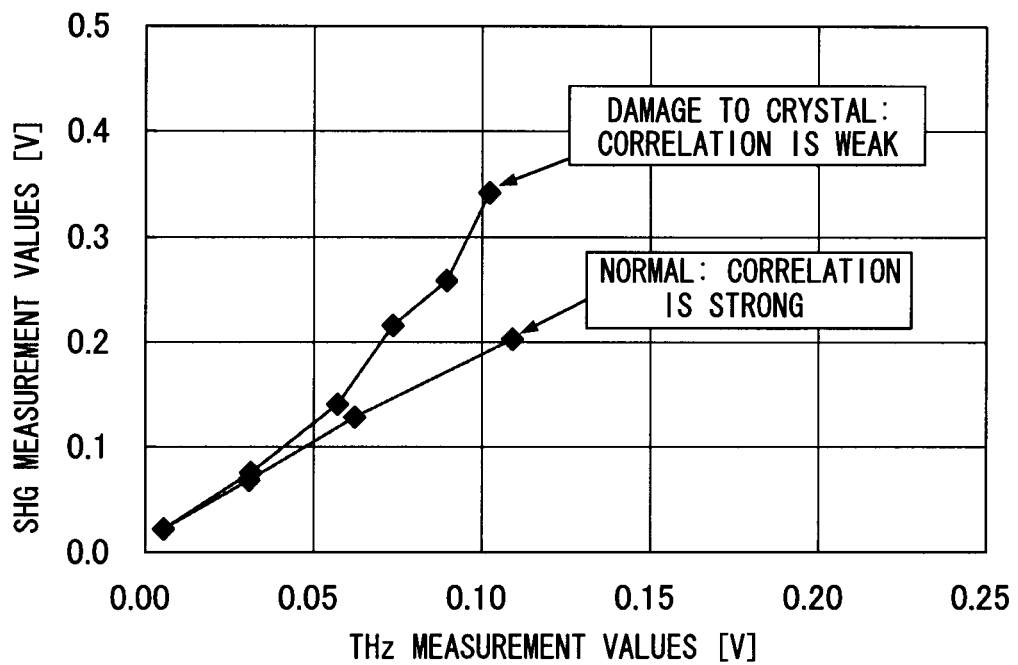
FIG. 11 is a graph showing the correlation between THz measurement values and SHG measurement values when a nonlinear optical crystal is normal and when it is damaged.

Through steps 110 to 114, the control unit 24 acquires the THz measurement values T and the SHG measurement values S. Next, in step 200, the control unit 24 computes an absolute value |R| of a correlation coefficient between the THz measurement values T and the SHG measurement values S acquired in step 114. As shown in FIG. 11, in a case where there is damage to the nonlinear optical crystal 12, the correlation between the THz measurement values T and the SHG measurement values S becomes weaker and the absolute value |R| of the correlation coefficient becomes smaller.

Therefore, in step 202, the control unit 24 determines whether or not the absolute value |R| of the correlation coefficient computed in step 200 exceeds a predetermined threshold value $th_1$ (e.g., 0.95). In a case where $|R|>th_1$, the control unit 24 determines that the correlation between the THz measurement values T and the SHG measurement values S is strong and that the nonlinear optical crystal 12 is normal and moves to step 116. Then, like in the first embodiment, the control unit 24 performs baseline correction in step 116, outputs the corrected measurement results in the next step 118, and thereafter ends the sample measurement processing.

In a case where $|R| \leq th_1$, the control unit 24 determines that the correlation between the THz measurement values T and the SHG measurement values S is weak and that there is damage to the nonlinear optical crystal 12 and moves to step 204. In step 204, the control unit 24 issues a notification that there is damage to the nonlinear optical crystal 12 by displaying on the display and operation unit 26 a message indicating that there is damage to the nonlinear optical crystal 12 or by outputting an audio message or beeping sound from an unillustrated speaker. Thereafter, the control unit 24 ends the sample measurement processing. In a case where $|R| \leq th_1$, the control unit 24 may also be configured to perform the processing of steps 116 and 118 as well as issue a notification that there is damage to the nonlinear optical crystal 12.

As described above, according to the terahertz spectrometry device pertaining to the second embodiment, whether or not there is damage to the nonlinear optical crystal can also be determined on the basis of the correlation between the THz waves and the SHG waves.

In the second embodiment, a case where the control unit 24 uses the absolute value of the correlation coefficient as an index expressing the correlation between the THz measurement values T and the SHG measurement values S was described, but the control unit 24 may also be configured to use a coefficient of determination to determine the correlation between the THz measurement values T and the SHG measurement values S. In this case, in step 200, the control unit 24 computes a coefficient of determination $R^2$. Like the absolute value |R| of the correlation coefficient, the coefficient of determination $R^2$ also becomes smaller in a case where the correlation between the THz measurement values T and the SHG measurement values S is weak. Therefore, in step 202, the control unit 24 determines whether or not the coefficient of determination $R^2$ exceeds a predetermined threshold value $th_2$ (e.g., 0.90). In a case where $R^2>th_2$, the control unit 24 determines that the nonlinear optical crystal 12 is normal. In a case where $R^2<th_2$, the control unit 24 determines that there is damage to the nonlinear optical crystal 12.

Next, a third embodiment will be described. In the third embodiment, a case where the terahertz spectrometry device determines whether or not there is damage to the nonlinear optical crystal on the basis of the correlation between the THz waves and the SHG waves obtained by a method differing from that of the second embodiment and thereafter performs terahertz spectrometry will be described. The configuration of the terahertz spectrometry device pertaining to the third embodiment is the same as the configuration of the terahertz spectrometry device 10 pertaining to the first embodiment, so the same reference signs will be assigned thereto and detailed description thereof will be omitted. The control unit 24 is an example of determining means of the present invention. The working of the terahertz spectrometry device pertaining to the third embodiment will be described below.

First, like in the first embodiment, the terahertz spectrometry device executes the baseline correction value calculation processing shown in FIG. 8 at a predetermined timing such as before sample measurement when the sample has not been set on the measurement stage 18. Further, in a normal condition in which there is no damage to the nonlinear optical crystal 12, the terahertz spectrometry device finds, by a processing step that is the same as step 200 of the sample measurement processing in the second embodiment, an absolute value |R'| of a correlation coefficient between the baseline THz measurement values and baseline SHG measurement values acquired in step 104 of the baseline correction value calculation processing and saves the absolute value |R'| in a predetermined storage region of the memory 36 or the like.

Figure 12:
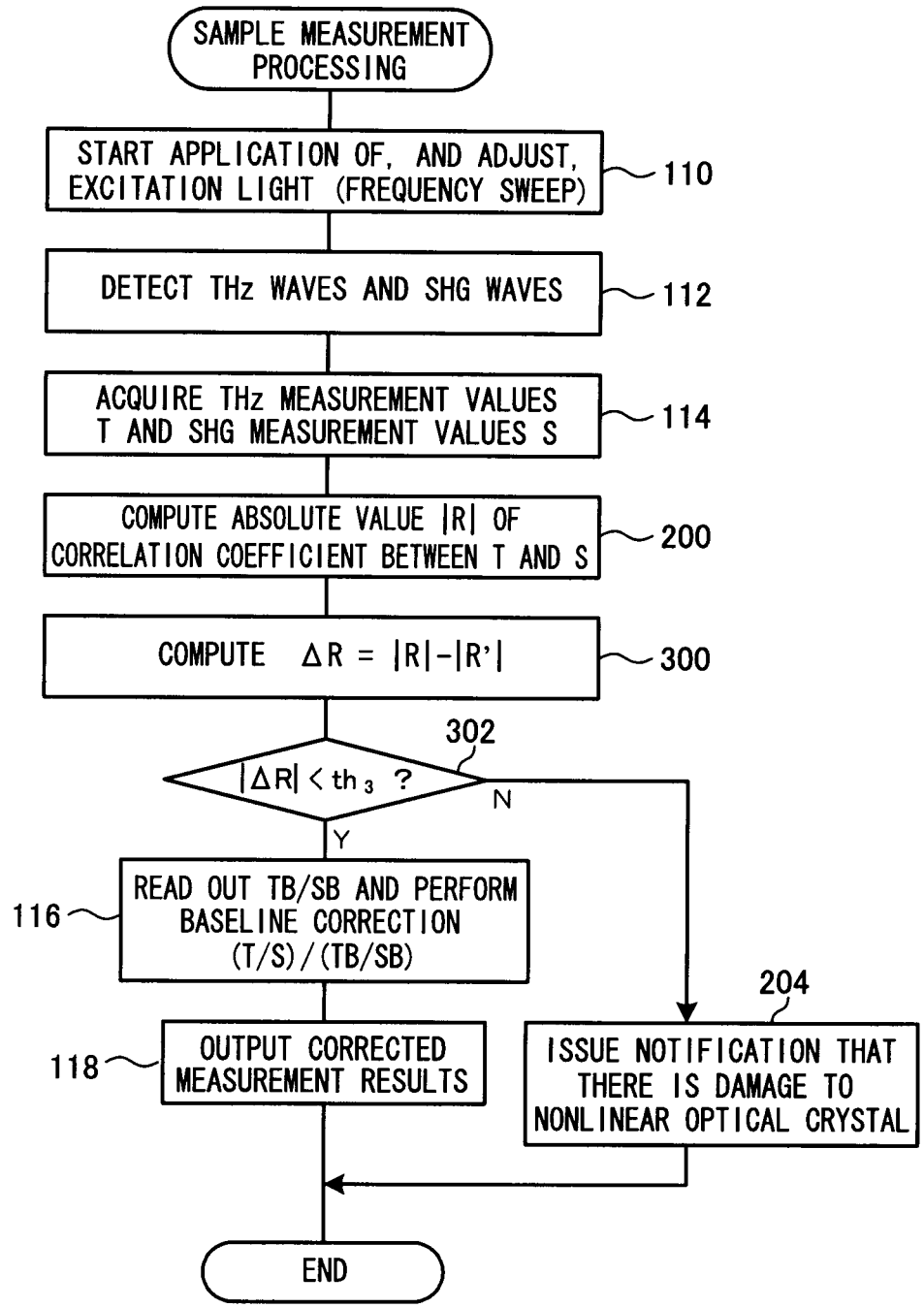
FIG. 12 is a flowchart showing the content of sample measurement processing in a third embodiment.

Then, the terahertz spectrometry device executes the sample measurement processing shown in FIG. 12 at the time of sample measurement when the sample has been set on the measurement stage 18. Each type of processing is performed as a result of the CPU 30 reading out and executing a program stored in the ROM 32. The sample measurement processing in the third embodiment will be described in detail below. In regard to processing steps that are the same as those of the sample measurement processing in the first and second embodiments, the same reference signs will be assigned thereto and detailed description thereof will be omitted.

Through steps 110 to 114 and 200, the control unit 24 computes the absolute value |R| of the correlation coefficient between the THz measurement values T and the SHG measurement values S.

Next, in step 300, the control unit 24 reads out the absolute value |R'| of the correlation coefficient between the baseline THz measurement values and the baseline SHG measurement values when the nonlinear optical crystal is normal which is stored in the predetermined region and computes a difference ΔR between |R| computed in step 200 and |R'|. When the nonlinear optical crystal 12 is normal, the baseline THz measurement values and the baseline SHG measurement values show a strong correlation, so the absolute value |R'| of the correlation coefficient becomes a large value. It is difficult to imagine that, in temporal changes thereafter, the absolute value |R| of the correlation coefficient will change in the direction in which it becomes even larger, so an increase in the difference ΔR means that the correlation between the THz measurement values and the SHG measurement values becomes weaker.

Therefore, in step 302, the control unit 24 determines whether or not an absolute value |ΔR| of the difference ΔR computed in step 300 is less than a predetermined threshold value $th_3$ (e.g., 0.05). In a case where |ΔR|≤$th_3$, the control unit 24 determines that the nonlinear optical crystal 12 is normal and executes the measurement processing of steps 116 and 118. In a case where |ΔR|≥$th_3$, the control unit 24 determines that there is damage to the nonlinear optical crystal 12 and moves to step 204. In step 204, the control unit 24 issues a notification that there is damage to the nonlinear optical crystal 12. Thereafter, the control unit 24 ends the sample measurement processing. In a case where |R|>$th_3$, the control unit 24 may also be configured to perform the processing of steps 116 and 118 as well as issue a notification that there is damage to the nonlinear optical crystal 12.

As described above, according to the terahertz spectrometry device pertaining to the third embodiment, whether or not there is damage to the nonlinear optical crystal can also be determined on the basis of the correlation between the THz waves and the SHG waves.

In the third embodiment, a case where the control unit 24 uses the difference between the absolute values of the correlation coefficient as an index expressing the correlation between the THz measurement values T and the SHG measurement values S was described, but the control unit 24 may also be configured to use a difference between coefficients of determination to determine the correlation between the THz measurement values T and the SHG measurement values S. In this case, in a normal condition in which there is no damage to the nonlinear optical crystal 12, the control unit 24 finds a coefficient of determination $R'^2$ between the baseline THz measurement values and the baseline SHG measurement values beforehand. Then, the control unit 24 computes a coefficient of determination $R^2$ in step 200 and computes a difference $\Delta R^2 (=R^2-R'^2)$ in step 300. Then, in step 302, the control unit 24 determines whether or not an absolute value |ΔR²| of the difference ΔR² is less than a predetermined threshold value $th_4$ (e.g., 0.10). In a case where |ΔR²|<$th_4$, the control unit 24 determines that the nonlinear optical crystal 12 is normal. In a case where |ΔR²|>$th_4$, the control unit 24 determines that there is damage to the nonlinear optical crystal 12.

Next, a fourth embodiment will be described. In the second and third embodiments, cases where the terahertz spectrometry device determines whether or not there is damage to the nonlinear optical crystal on the basis of the correlation between the THz waves and the SHG waves were described, but in the fourth embodiment, a case where the terahertz spectrometry device determines whether or not there is damage to the nonlinear optical crystal on the basis of whether or not the intensity of the THz waves and the intensity of the SHG waves that have been detected are obtained as values according to a relational equation between the THz waves and the SHG waves when the nonlinear optical crystal is in a normal condition will be described.

The configuration of the terahertz spectrometry device pertaining to the fourth embodiment is the same as the configuration of the terahertz spectrometry device 10 pertaining to the first embodiment, so the same reference signs will be assigned thereto and detailed description thereof will be omitted. The control unit 24 is an example of determining means of the present invention. The working of the terahertz spectrometry device pertaining to the fourth embodiment will be described below.

First, like in the first embodiment, the terahertz spectrometry device executes the baseline correction value calculation processing shown in FIG. 8 at a predetermined timing such as before sample measurement when the sample has not been set on the measurement stage 18. Further, the terahertz spectrometry device finds a relational equation between the THz measurement values and the SHG measurement values such as shown in FIG. 3 using the baseline THz measurement values and baseline SHG measurement values acquired in step 104 of the baseline correction value calculation processing in a normal condition in which there is no damage to the nonlinear optical crystal 12 and saves the relational equation in a predetermined storage region of the memory 36 or the like. As shown in FIG. 11, in a case where there is damage to the nonlinear optical crystal 12, the correlation between the THz measurement values and the SHG measurement values becomes weaker compared to when the nonlinear optical crystal 12 is normal. The terahertz spectrometry device uses the relational equation between the THz measurement values and the SHG measurement values to grasp this change and determine whether or not there is damage to the nonlinear optical crystal 12. As the relational equation, the terahertz spectrometry device can use an approximation such as linear approximation or polynomial approximation.

Figure 13:
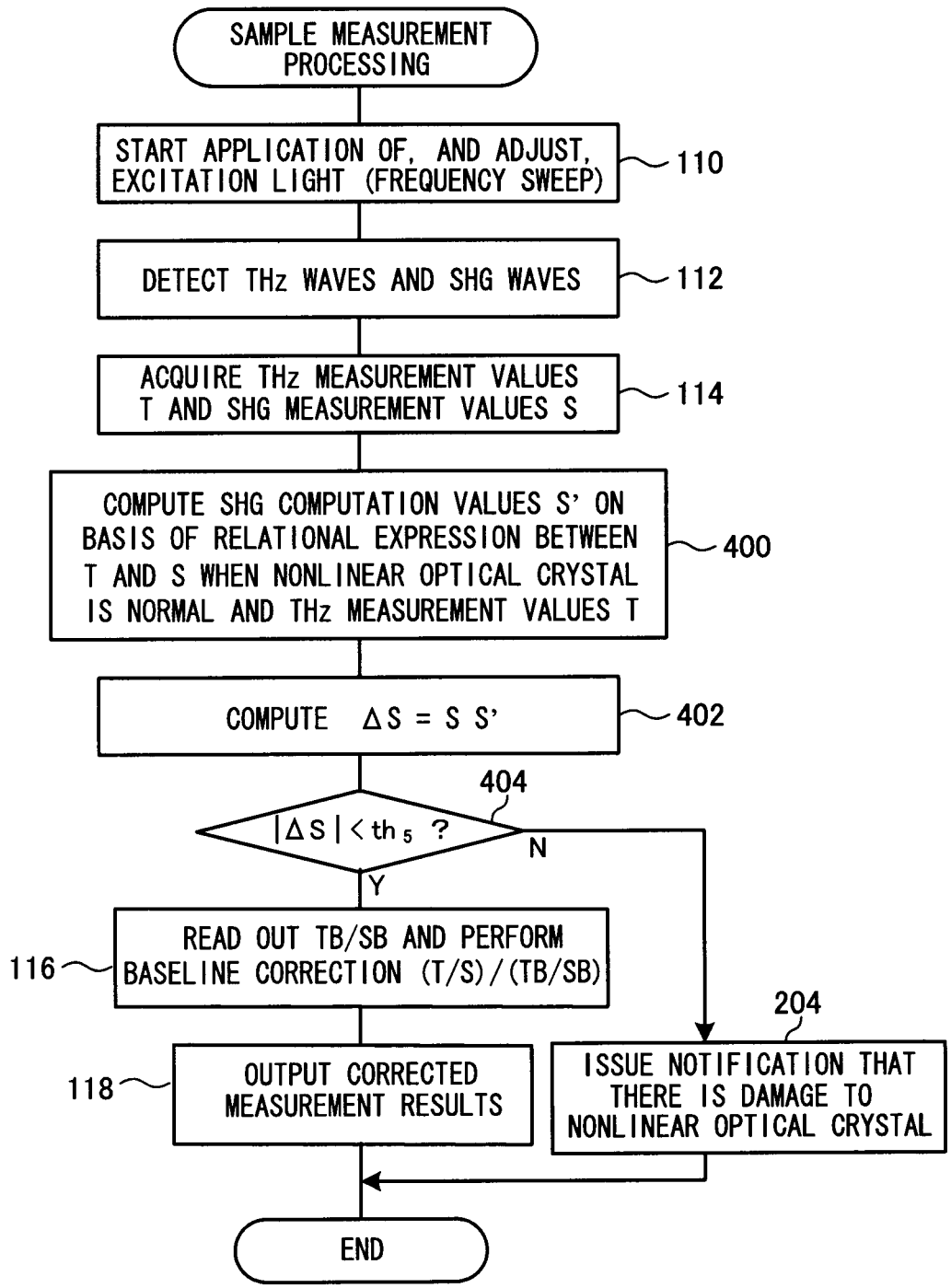
FIG. 13 is a flowchart showing the content of sample measurement processing in a fourth embodiment.

Then, the terahertz spectrometry device executes the sample measurement processing shown in FIG. 13 at the time of sample measurement when the sample has been set on the measurement stage 18. Each type of processing is performed as a result of the CPU 30 reading out and executing a program stored in the ROM 32. The sample measurement processing in the fourth embodiment will be described in detail below. In regard to processing steps that are the same as those of the sample measurement processing in the first and second embodiments, the same reference signs will be assigned thereto and detailed description thereof will be omitted.

Through steps 110 to 114, the control unit 24 acquires the THz measurement values T and the SHG measurement values S. Next, in step 400, the control unit 24 reads out the relational equation between the THz measurement values and the SHG measurement values when the nonlinear optical crystal 12 is normal from the predetermined storage region, computes values of the SHG measurement values imagined in a case where the nonlinear optical crystal 12 is normal on the basis of the relational equation and the THz measurement values T acquired in step 114, and denotes the values as SHG computed values S'.

Figure 14:
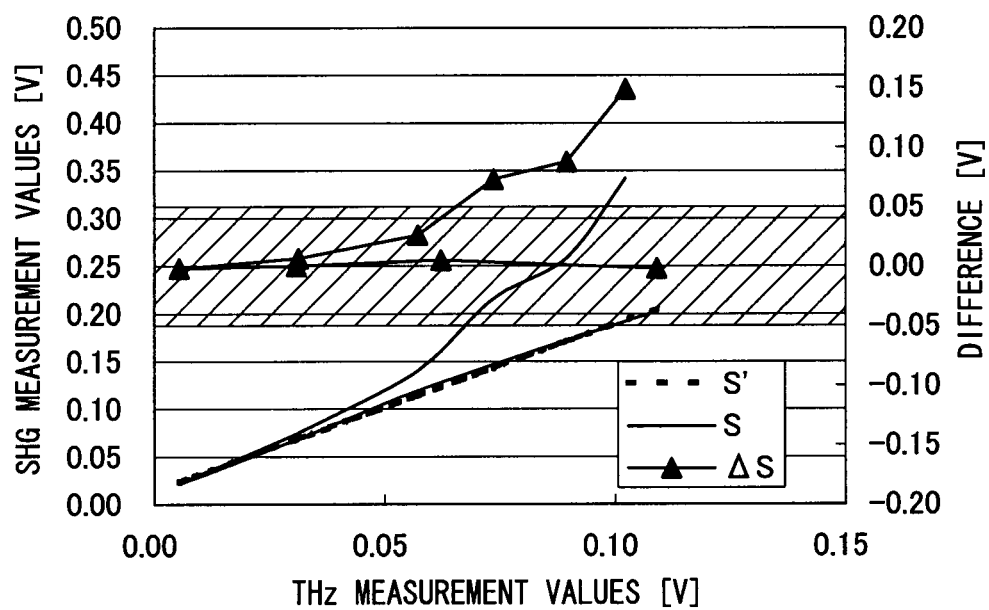
FIG. 14 is a graph showing the correlation between THz measurement values and SHG measurement values and the differences between SHG measurement values and SHG computed values.

Next, in step 402, the control unit 24 computes a difference ΔS between the SHG measurement values S acquired in step 114 and the SHG computed values S' computed in step 400. As shown in FIG. 14, an increase in the difference ΔS means that the correlation between the THz measurement values and the SHG measurement values becomes weaker.

Therefore, in step 404, the control unit 24 determines whether or not an absolute value |ΔS| of the difference ΔS computed in step 402 is less than a predetermined threshold value $th_5$ (e.g., 0.05 V). In a case where |ΔS|<$th_5$, the control unit 24 determines that the nonlinear optical crystal 12 is normal and executes the measurement processing of steps 116 and 118. In a case where |ΔS|>$th_5$, the control unit 24 determines that there is damage to the nonlinear optical crystal 12 and moves to step 204. In step 204, the control unit 24 issues a notification that there is damage to the nonlinear optical crystal 12. Thereafter, the control unit 24 ends the sample measurement processing. In a case where |ΔS|<$th_5$, the control unit 24 may also be configured to perform the processing of steps 116 and 118 as well as issue a notification that there is damage to the nonlinear optical crystal 12.

As described above, according to the terahertz spectrometry device pertaining to the fourth embodiment, the control unit 24 can determine whether or not there is damage to the nonlinear optical crystal not only on the basis of the correlation between the THz waves and the SHG waves but also on the basis of the difference between the detected THz measurement values and the relational equation between the THz measurement values and the SHG measurement values when the nonlinear optical crystal is normal.

In the fourth embodiment, a case where the control unit 24 determines whether or not there is damage to the nonlinear optical crystal using the difference ΔS between the SHG measurement values S and the SHG computed values S' was described, but the control unit 24 may also be configured to determine whether or not there is damage to the nonlinear optical crystal using a difference ΔT between the THz measurement values T and THz computed values T'. In this case, in step 400, the control unit 24 computes, as the THz computed values T', values of the THz measurement values imagined in a case where the nonlinear optical crystal 12 is normal on the basis of the relational equation when the nonlinear optical crystal 12 is normal and the SHG measurement values S acquired in step 114. In step 402, the control unit 24 computes the difference ΔT between the THz measurement values T acquired in step 114 and the THz computed values T' computed in step 400. Then, in step 404, the control unit 24 determines whether or not an absolute value |ΔT| of the difference ΔT is less than a predetermined threshold value $th_6$ (e.g., 0.05 V). In a case where $|ΔT|<th_6$, the control unit 24 determines that the nonlinear optical crystal 12 is normal. In a case where $|ΔT|>th_6$, the control unit 24 determines that there is damage to the nonlinear optical crystal 12.

Next, a fifth embodiment will be described. In the fifth embodiment, an inspection device that inspects the condition of the nonlinear optical crystal will be described. The configuration of the nonlinear optical crystal inspection device pertaining to the fifth embodiment is the same as the configuration of the terahertz spectrometry device 10 pertaining to the first embodiment, so the same reference signs will be assigned thereto and detailed description thereof will be omitted. The working of the inspection device pertaining to the fifth embodiment will be described below.

Figure 15:
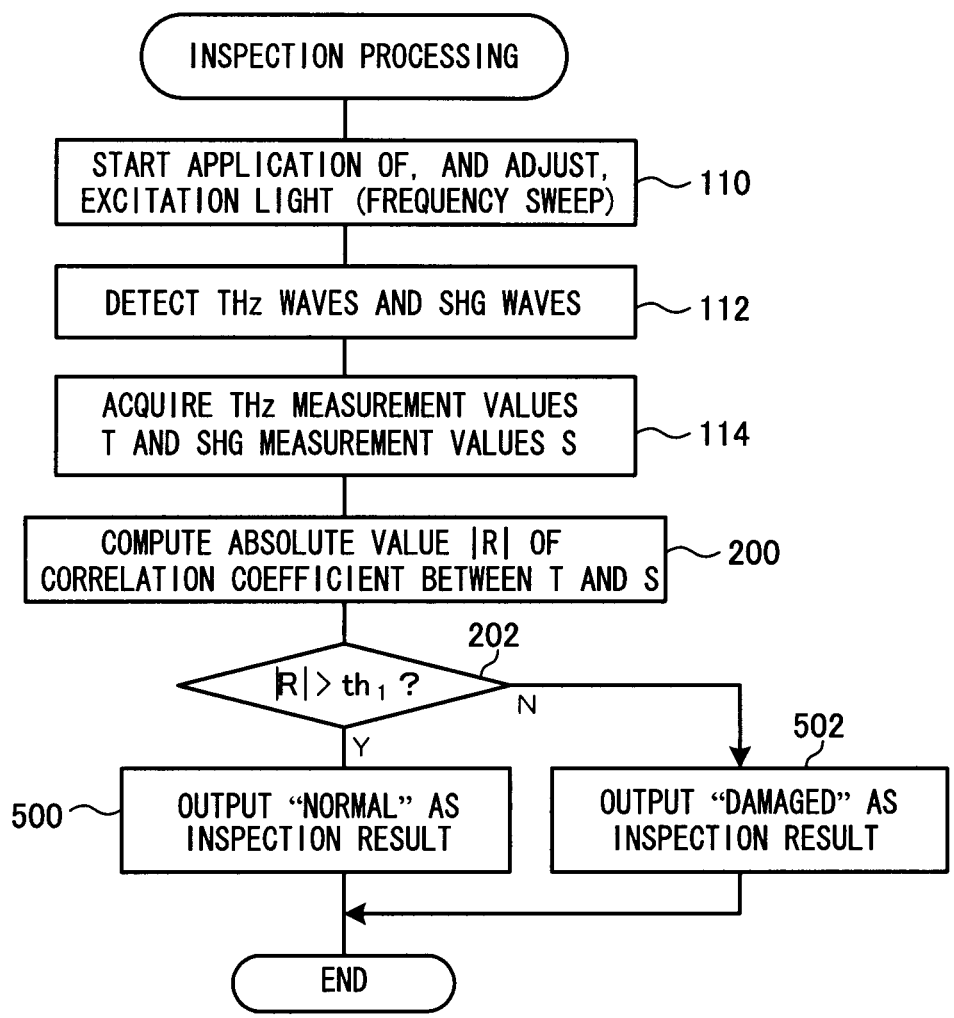
FIG. 15 is a flowchart showing the content of inspection processing in a fifth embodiment.

Inspection processing executed in the nonlinear optical crystal inspection device pertaining to the fifth embodiment will be described with reference to FIG. 15. The inspection processing is performed as a result of the CPU 30 reading out and executing a program stored in the ROM 32. In regard to processing steps in the inspection processing pertaining to the fifth embodiment that are the same as those of the sample measurement processing in the first and second embodiments, the same reference signs will be assigned thereto and detailed description thereof will be omitted.

Through steps 110 to 114 and 200, the control unit 24 computes the absolute value |R| of the correlation coefficient between the THz measurement values T and the SHG measurement values S. Next, in step 202, the control unit 24 determines whether or not $|R|>th_1$. In a case where $|R|>th_1$, the control unit 24 determines that the correlation between the THz measurement values T and the SHG measurement values S is strong and that the nonlinear optical crystal 12 is normal and moves to step 500. In step 500, the control unit 24 outputs "normal" as the inspection result. Thereafter, the control unit 24 ends the inspection processing. In a case where $|R|<th_1$, the control unit 24 determines that the correlation between the THz measurement values T and the SHG measurement values S is weak and that there is damage to the nonlinear optical crystal 12 and moves to step 502. In step 502, the control unit 24 outputs "damaged" as the inspection result. Thereafter, the control unit 24 ends the inspection processing.

As described above, according to the nonlinear optical crystal inspection device pertaining to the fifth embodiment, the condition of the nonlinear optical crystal can be inspected on the basis of the correlation between the THz waves and the SHG waves.

In the fifth embodiment, a case where, like in the second embodiment, the inspection device uses the absolute value of the correlation coefficient as an index indicating the correlation between the THz measurement values T and the SHG measurement values S was described, but the inspection device may also be configured to inspect the condition of the nonlinear optical crystal using the same method as in the third or fourth embodiment.

Further, in each of the above embodiments, a case where the present invention uses the SHG waves as the reference light was described, but the reference light is not limited to this. It suffices for the reference light to be an optical harmonic that has been frequency converted in accordance with the nonlinear coefficient that the nonlinear optical crystal has. For example, the present invention may also use the third harmonic.

Further, in each of the above embodiments, a case where the present invention performs terahertz spectrometry using a frequency sweep was taken as an example and described, but the present invention can also be applied to the case of measurement resulting from THz waves of a specific frequency. In this case, the processing that was performed for each frequency in the above embodiments is performed only in regard to the specific frequency.

Further, in each of the above embodiments, a case where the terahertz spectrometry device of the present invention is realized as a result of the CPU executing a program was described, but it is also possible to realize the terahertz spectrometry device using a semiconductor integrated circuit such as an application-specific integrated circuit (ASIC).

What is claimed is:

1. A terahertz spectrometry device comprising:
    a nonlinear optical crystal that has a unique nonlinear coefficient and generates, from light beams of two different wavelengths made incident thereon, terahertz waves resulting from sum frequency generation or difference frequency generation according to the nonlinear coefficient and optical harmonics in which the light beams of two different wavelengths have been wavelength converted in accordance with the nonlinear coefficient;
    first detecting means that directly detects the terahertz waves generated from the nonlinear optical crystal or detects measurement terahertz waves that have passed through or been reflected from a measurement target to which the terahertz waves have been applied;
    second detecting means that detects at least one of the optical harmonics generated from the nonlinear optical crystal; and
    measuring means that obtains measurement values in which an intensity of the measurement terahertz waves detected by the first detecting means has been corrected on the basis of an intensity of the at least one optical harmonic detected by the second detecting means.

2. The terahertz spectrometry device according to claim 1, wherein the measuring means acquires, as baseline terahertz waves, terahertz waves directly detected by the first detecting means, acquires, as a baseline optical harmonic, an optical harmonic detected at the same time as the baseline terahertz waves, and obtains the corrected measurement values on the basis of a relationship between the baseline terahertz waves, the baseline optical harmonic, the measurement terahertz waves, and the optical harmonic detected at the same time as the measurement terahertz waves.

3. The terahertz spectrometry device according to claim 1, wherein the optical harmonic is a second harmonic of the light beams of two different wavelengths.

4. The terahertz spectrometry device according to claim 1, wherein the measuring means obtains the measurement values using the measurement terahertz waves detected by applying the terahertz waves generated from the nonlinear optical crystal to the measurement target while performing a frequency sweep or the measurement terahertz waves detected by applying terahertz waves of a specific frequency generated from the nonlinear optical crystal to the measurement target.

5. The terahertz spectrometry device according to claim 1, further comprising determining means that determines whether or not there is damage to the nonlinear optical crystal on the basis of a correlation between the intensity of the measurement terahertz waves detected by the first detecting means and the intensity of the at least one optical harmonic detected by the second detecting means.

6. The terahertz spectrometry device according to claim 5, wherein the determining means determines that there is damage to the nonlinear optical crystal in a case where an absolute value of a correlation coefficient, or a coefficient of determination, between the intensity of the measurement terahertz waves detected by the first detecting means and the intensity of the at least one optical harmonic detected by the second detecting means is smaller than a predetermined threshold value.

7. The terahertz spectrometry device according to claim 5, wherein the determining means determines that there is damage to the nonlinear optical crystal in a case where a difference between an absolute value of a correlation coefficient, or a coefficient of determination, between the intensity of the measurement terahertz waves detected by the first detecting means and the intensity of the at least one optical harmonic detected by the second detecting means and an absolute value of a correlation coefficient, or a coefficient of determination, obtained using the nonlinear optical crystal in a normal condition is larger than a predetermined threshold value.

8. The terahertz spectrometry device according to claim 1, further comprising determining means that determines that there is damage to the nonlinear optical crystal in a case where a difference between either one intensity of the intensity of the measurement terahertz waves detected by the first detecting means and the intensity of the at least one optical harmonic detected by the second detecting means, a computed value representing the other intensity obtained on the basis of a relational expression between the intensity of the measurement terahertz waves and the intensity of the at least one optical harmonic obtained using the nonlinear optical crystal in a normal condition, and the other intensity that has been detected is larger than a predetermined threshold value.

9. A terahertz spectrometry method comprising:
  detecting measurement terahertz waves that have passed through or been reflected from a measurement target to which have been applied terahertz waves generated from a nonlinear optical crystal that has a unique nonlinear coefficient and generates, from light beams of two different wavelengths made incident thereon, terahertz waves resulting from sum frequency generation or difference frequency generation according to the nonlinear coefficient and optical harmonics in which the light beams of two different wavelengths have been wavelength converted in accordance with the nonlinear coefficient;
  detecting at least one of the optical harmonics generated from the nonlinear optical crystal; and
  obtaining measurement values in which an intensity of the measurement terahertz waves that have been detected has been corrected on the basis of an intensity of the at least one optical harmonic that has been detected.

10. A nonlinear optical crystal inspection device comprising:
  a nonlinear optical crystal that has a unique nonlinear coefficient and generates, from light beams of two different wavelengths made incident thereon, terahertz waves resulting from sum frequency generation or difference frequency generation according to the nonlinear coefficient and optical harmonics in which the light beams of two different wavelengths have been wavelength converted in accordance with the nonlinear coefficient;
  first detecting means that directly detects the terahertz waves generated from the nonlinear optical crystal or detects measurement terahertz waves that have passed through or been reflected from a measurement target to which the terahertz waves have been applied;
  second detecting means that detects at least one of the optical harmonics generated from the nonlinear optical crystal; and
  determining means that determines whether or not there is damage to the nonlinear optical crystal on the basis of a correlation between an intensity of the measurement terahertz waves detected by the first detecting means and an intensity of the at least one optical harmonic detected by the second detecting means.

11. A nonlinear optical crystal inspection method comprising:
  detecting measurement terahertz waves that have passed through or been reflected from a measurement target to which have been applied terahertz waves generated from a nonlinear optical crystal that has a unique nonlinear coefficient and generates, from light beams of two different wavelengths made incident thereon, terahertz waves resulting from sum frequency generation or difference frequency generation according to the nonlinear coefficient and optical harmonics in which the light beams of two different wavelengths have been wavelength converted in accordance with the nonlinear coefficient;
  detecting at least one of the optical harmonics generated from the nonlinear optical crystal; and
  determining whether or not there is damage to the nonlinear optical crystal on the basis of a correlation between an intensity of the measurement terahertz waves that have been detected and an intensity of the at least one optical harmonic that has been detected.

* * * * *